United States Patent
Kunze

(10) Patent No.: US 7,544,920 B2
(45) Date of Patent: Jun. 9, 2009

(54) CONTROLLER FOR AN ELECTRONIC LINE-SCAN CAMERA WHICH HAS AT LEAST TWO LINES OF LIGHT-SENSITIVE PIXELS

(75) Inventor: Joerg Kunze, Ahrensburg (DE)

(73) Assignee: Basler AG, Ahrensburg (DE)

( * ) Notice: Subject to any disclaimer, the term of this patent is extended or adjusted under 35 U.S.C. 154(b) by 10 days.

(21) Appl. No.: 11/876,008

(22) Filed: Oct. 22, 2007

(65) Prior Publication Data

US 2008/0099663 A1 May 1, 2008

(30) Foreign Application Priority Data

Nov. 1, 2006 (DE) .................. 10 2006 051 950

(51) Int. Cl.
*H01L 27/00* (2006.01)

(52) U.S. Cl. .................. 250/208.1; 250/214 R

(58) Field of Classification Search ............. 250/208.1, 250/214 R, 214 P, 214.1; 348/88, 130–132, 348/125, 206, 312–314, 322, 142; 396/20, 396/215

See application file for complete search history.

(56) References Cited

U.S. PATENT DOCUMENTS 6,028,630 A    2/2000   Fukui et al.
7,425,982 B2 * 9/2008   Joskin et al. ............... 348/142

FOREIGN PATENT DOCUMENTS

JP    56-017572 A    2/1981
JP    02-306378 A   12/1990

* cited by examiner

*Primary Examiner*—Que T Le
(74) *Attorney, Agent, or Firm*—Howson & Howson LLP

(57) ABSTRACT

A method for controlling an electronic line-scan camera having at least two lines with light-sensitive pixels by means of external trigger signals. A predetermined number of lines of the sensor are exposed due to a first external trigger signal and the image information of the first exposed line and that of the subsequent line or lines are each output successively.

13 Claims, 1 Drawing Sheet

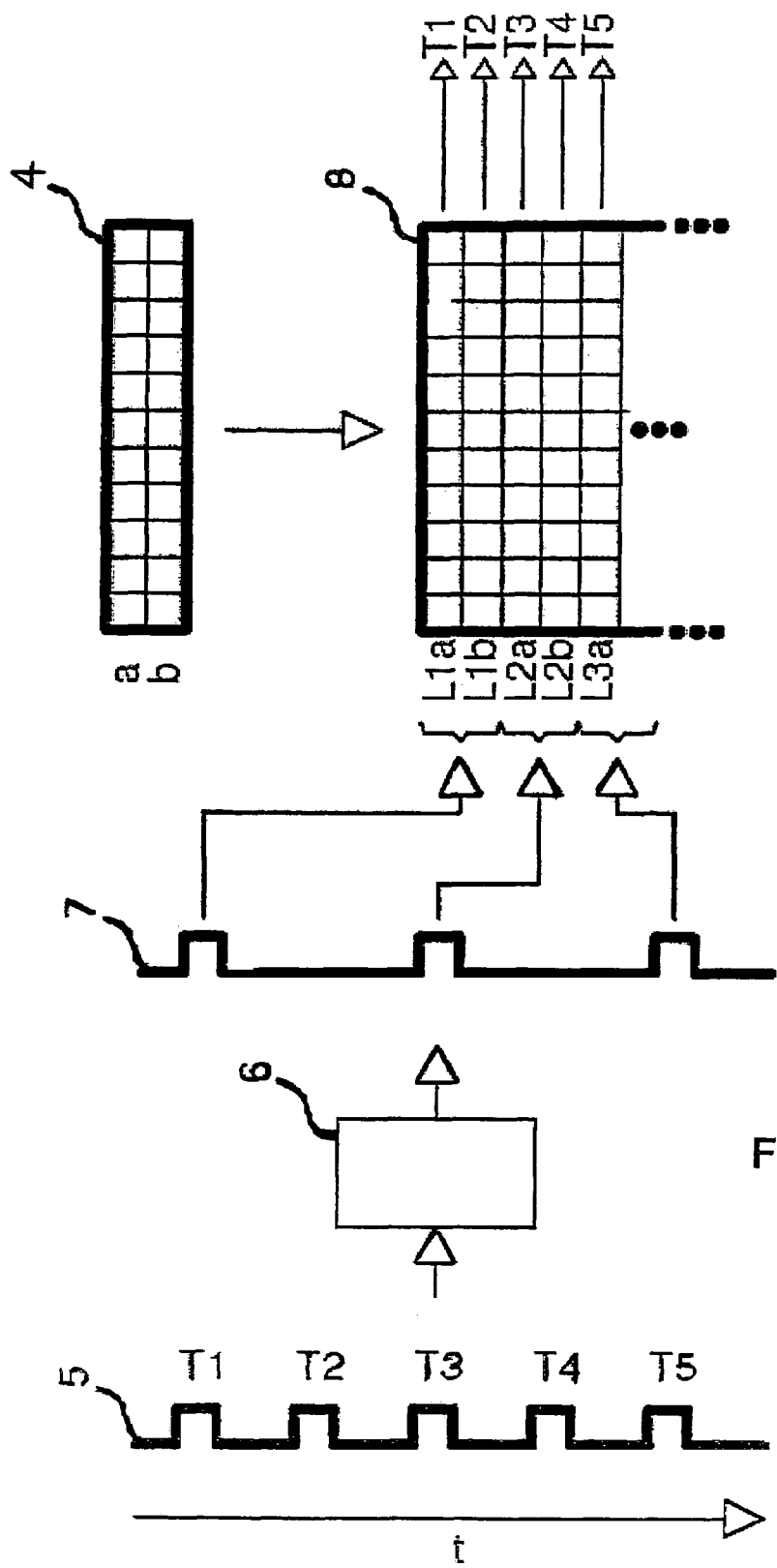
FIGURE

CONTROLLER FOR AN ELECTRONIC LINE-SCAN CAMERA WHICH HAS AT LEAST TWO LINES OF LIGHT-SENSITIVE PIXELS

BACKGROUND OF THE INVENTION

The invention relates to a method for controlling an electronic line-scan camera, which has at least two lines with light-sensitive pixels, by means of external trigger signals.

It is known to scan continuous production processes or moving objects optically by means of line-scan cameras. Here, the camera and the object move relative to each other, with the motion taking place perpendicular to the sensor lines. Usually, the process takes place such that a trigger signal is generated as a function of the motion of the object, with the electronic camera being triggered by this trigger signal at certain sections of the object or certain times. A linear image is generated. Through successive linear scanning and assembly of several successive image lines in series, the entire object can be scanned and imaged.

For line-scan cameras with only one line, a trigger signal triggers exposure of the entire line, and then the image information is output. In principle, the control of such a line-scan camera presents no problems. Each line is allocated to a certain linear area on the object to be scanned. Control is performed such that the image lines are scanned at identical spatial intervals. Therefore, the spatial resolution is independent of the relative speed between the object and camera. The function of the trigger consists in the correct alignment of the camera to the relative motion between the camera and object. It must be guaranteed that the camera records an image at each trigger signal. Otherwise distortion could be generated. For optimal alignment, an overall image with isotropic resolution can be assembled line by line.

In line-scan cameras, sometimes multiple-line sensors are also used. These feature a predetermined number of sensor lines. Here, all of the lines are exposed simultaneously according to an external trigger signal. Usually a wider image area is detected than in a single-line image sensor. For the same spatial resolution, it would then be necessary to generate farther trigger signals spaced farther apart. However, because the trigger signals are generated external to the camera on the object side, an arbitrary use of such electronic cameras is not always easily possible.

SUMMARY OF THE INVENTION

Therefore, the invention is based on the problem of constructing a controller for an electronic multiple-line line-scan camera, so that triggering as in a line-scan camera with a single-line sensor is possible.

The problem is solved according to the invention in that, based on a first external trigger signal, a predetermined number of lines is exposed and the image information of the first exposed line, and the subsequent line or lines are each output successively. Here, an exposed line should be understood to be a line provided for exposure and whose image information is read out or output after the exposure.

In particular, it can be provided that, on the basis of subsequent external trigger signals, the image information of each subsequent line is output. Then the multiple-line line-scan camera behaves like a single-line line-scan camera because for each subsequent external trigger signal, the image information of one line is output, which also corresponds to a subsequently recorded linear region of the object.

In particular, it can also be provided that the external trigger signals are counted and an external trigger signal is set as a first trigger signal triggering the exposure of the lines when the number of counted external trigger signals corresponds to the number of exposed lines. In this way, all of the image information of one recording is output, and a new exposure of the lines is performed only on the basis of a subsequent first trigger signal.

The subsequent trigger signals cause only one output of the information of the subsequent image lines of the sensor or the camera, which have been exposed based on the first trigger signal. Consequently, for example, for a two-line camera, every second external trigger signal, and for a four-line camera, every fourth external trigger signal, is set as a first trigger signal. Only the first trigger signal set by the controller causes all of the lines of the camera to be exposed. The external trigger signals in-between cause an output of the image information of the relevant image lines of the camera. Through such control, image information of only one line is output due to each external trigger signal, although several lines of the camera have been exposed. Thus, it is possible to control a multiple-line electronic camera in the same way as a single-line line-scan camera. Therefore, the installation of such a camera, for example, as a replacement for a defect camera, is significantly simplified.

A special advantage of the invention is that a camera with multiple lines controlled in this way operates significantly faster than a single-line line-scan camera. For a single-line line-scan camera, the image information is read out and then output after each exposure. According to the invention, it is provided that all of the exposed lines are read out after an exposure. The image information of the individual lines is stored or held according to the sensor construction until it is retrieved and output line by line. This can be performed in succession either based on subsequent trigger signals or automatically. The read-out process is frequently the limiting time factor in single-line line-scan cameras. Because the lines in multiple-line line-scan cameras can be read out in parallel time-wise, the image information of several successive lines is available after only one read-out process. Accordingly, the output can be performed more quickly. Here it is possible to start the exposure while the read-out or output process is still running.

It is useful when a new exposure of the lines of the sensor is performed after a number of trigger signals corresponding to the number of lines exposed after the preceding first trigger signal. It is also useful when the image information of an exposed line for output is stored or held based on the trigger signal allocated to the line. Then the multiple-line line-scan camera behaves on the user side like a single-line line-scan camera.

Through the control according to the invention, the image information of one line is output on the basis of each external trigger signal. The special feature consists in that, for an n-line camera, only every nth external trigger signal leads to an exposure of the light-sensitive lines. The external trigger signals lying in-between are used, in particular, for retrieving the image information of the lines that have been previously already exposed and allocated to the relevant trigger signals. With the control according to the invention, multiple-line line-scan cameras can be controlled so that they behave like single-line line-scan cameras on the user side. The number of exposed lines, whose image information has been retrieved, can correspond to or be less than the number of lines of the sensor. In addition, it is possible to increase the image capture rate, because the image information becomes available more quickly.

With this control, it is correspondingly possible to use a multiple-line line-scan camera instead of a single-line line-scan camera. Because the camera is controlled in the same way as in a single-line line-scan camera, no other type of trigger signal or especially adapted trigger signal must be generated. The external trigger signals, which are generated on the object side or on the user side and which are not set as the first trigger signals, can be used or rejected for line-by-line output of the image information. After all of the lines have been read out, the next external trigger signal is set as a first trigger signal, which triggers an exposure of all of the lines of the camera provided for exposure. The subsequent external trigger signals do not cause a new exposure of the camera or its sensor but instead only the line-by-line output of the image information of the already exposed lines. Consequently, the output of the image information also matches that of a single-line line-scan camera. Therefore, a multiple-line line-scan camera can be easily integrated into existing systems, for example, into production lines.

BRIEF DESCRIPTION OF THE DRAWINGS

The invention will be explained in more detail below with reference to the drawing: FIGURE schematically shows the control for a two-line sensor according to the invention.

DETAILED DESCRIPTION OF THE INVENTION

In the drawing, the signal flow for controlling an electronic camera is shown schematically. In the embodiment shown, for example, due to the motion of an object, external trigger signals T1, T2 . . . T5 following each other spatially are generated. These trigger signals can be, for example, feed-controlled, if the object to be scanned is moved and is located, for example, on an assembly line. An image line should be recorded at each of these external trigger signals 5. For uniformly moving objects, time-controlled trigger signals can also be used, which feature a time interval relative to each other. Usually, the trigger signals are generated continuously, so that a linear region of the object to be scanned is allocated to each trigger signal, with this region being adjacent to a directly adjacent linear region allocated to the previous trigger signal. Thus, the assembled image lines form the overall image of the object.

The image sensor 4 of the electronic camera is formed as a two-line sensor with two lines a, b. The lines a, b run parallel to each other and feature a plurality of light-sensitive pixels, of which only a few are shown in the drawing. The optics of the camera are constructed and aligned so that each line a, b to be exposed detects a different linear area of the object to be recorded. Each recorded area lies directly adjacent to each other.

For a single-line image sensor, due to an external trigger signal, one line is exposed, and its image information is output to the image processor. To allow a multiple-line line-scan camera to be controlled also with such trigger signals, like those used for single-line line-scan cameras, a controller 6 is provided, whose function is described below.

In the start-up state, both lines a, b of the line-scan camera are not exposed. Due to the first external trigger signal T1, both lines a, b of the image sensor 4 are exposed. After exposure, the image information L1a of the first exposed line a is output. This is shown schematically in the drawing by the arrow T1. Due to the subsequent external trigger signal T2, the image information L1b of the second, already exposed line b is output. Then all of the image information of the two-line image sensor has been output.

In principle, it can be provided that an exposure is also performed at the trigger T2. The recorded information, however, is not used.

The next external trigger signal T3 is set by the controller 6 as a first trigger signal, and both image lines a, b of the image sensor 4 are exposed again. After the exposure, based on the trigger signal T3, the image information L2a of the first, newly exposed line a is output. The following external trigger signal T4 leads to the output of the image information L2b of the second, then already exposed line b.

The subsequently following external trigger signal T5 is set like the trigger signals T3 and T1 as a first external trigger signal and leads to a new exposure of both sensor lines a, b. The output is performed as in the preceding exposure period.

The controller 6 consequently has the effect that for a two-line sensor with two sensor lines a, b, only every second external trigger signal T1, T3, T5 leads to an exposure of both image lines. The external trigger signals T2, T4 in-between control the output of the image information of the second image line b. From the external trigger signals 5, a new set of trigger signals 7 is generated internal to the camera, whose intervals between each other in the time direction t or motion direction of the object are greater than those of the external trigger signals and which each trigger an exposure of both image lines. The intervals of the generated first trigger signals or the trigger signals, which are set as first trigger signals, equals, in particular, a multiple of the intervals of the external trigger signals. The multiple here corresponds to the number of exposed lines a, b. The controller can comprise a counter, which sets an external trigger signal as a first trigger signal or generates a first trigger signal, when the number of external trigger signals corresponds to the number of previously exposed lines. A first trigger signal can then also be generated when the image information of all of the exposed image lines has been read out.

Consequently, the camera or its image sensor 4 need be exposed only once for the output of two image lines. The second image line b already contains the image information that was retrieved first on the basis of the second external trigger signal T2, T4. Consequently, only a one-time readout of the information of the pixels need be performed, while the image information is then output line by line, for example, on the basis of a subsequent trigger signal T2, T4.

It is useful to ensure that the trigger signals are generated according to the precise spatial allocation of the object to be recorded and the generated image lines. If the intervals between trigger signals are too large and also correspond to a larger spatial interval of the lines to be recorded for moving objects, the image information of the already recorded second image lines b would no longer fit the image that is to be recorded at the time of the second trigger signal T2. Usually, it is provided that the image information of the second image line b is buffered or held until it is output at the subsequent trigger signal. If the interval of the trigger signals is too large, it can be provided that the buffered image information is rejected, in order to then re-record a current image region for a following external trigger signal.

Accordingly, the controller according to the invention can be used preferably for providing external trigger signals, which have an equal spatial interval relative to each other, such that the lines of the object to be imaged lie spatially directly next to each other. In addition, if the external trigger signals are generated with a spatial and/or temporal interval relative to each other, through which for a single-line sensor, lines of the object lying directly one next to the other are scanned, the same image can be recorded by the multiple-line sensor. Such trigger signals are usually generated on the user side.

Often, the trigger signals T1, T2 . . . T5 are generated as a function of the position of the object to be scanned relative to the camera. At the trigger signal T1, a first image line is recorded by the first sensor line a. At the time of the second trigger signal T2, a line of the object should be recorded, which has already been recorded at the time of the first trigger signal T1 by the second sensor line b. Because it has already been exposed at the first trigger signal T1, at the second trigger signal T2, only the image data of the second line must be output, without which a new exposure would become necessary. The corresponding applies to the following exposure period at the trigger signals T3, T4.

Such a controller allows the use of multiple-line line-scan cameras instead of single-line line-scan cameras, without changing the external control signals and without adapting the image-processing system to the output of the camera. The effect is that after an external trigger signal, the image information of one line can always be read out at the output of the camera. Here, it is not significant how many sensor lines the image sensor actually has. For a three-line sensor, only every third trigger signal and for an n-line sensor, every nth external trigger signal is set as a first trigger signal and leads to an exposure of the lines. Nevertheless, after each external trigger signal, the image information of only one line is output.

The successive image information is output line by line as in a single-line line-scan camera. A total image 8 is produced, which is assembled from the individual image lines L1a, L1b, L2a, L2b . . . . At each trigger signal T1-T5, the image information of one line is output. The multiple-line line-scan camera consequently behaves like a single-line line-scan camera both from the control by the trigger signals and also from the output of the image information due to the trigger signals.

The invention was explained above with reference to a camera with several lines. Naturally, it is also possible that the control and the method for a camera are used, which has several sensors each with one line with light-sensitive pixels. It is essential that the invention allows the use of multiple-line line-scan cameras in cases in which the trigger signals generated external to the camera and/or the external image processing are adapted to a single-line line-scan camera.

The invention claimed is:

1. A method for controlling an electronic line-scan camera, which has at least two lines with light-sensitive pixels, by means of successive external trigger signals, comprising the steps of:
    exposing a predetermined number of lines of the camera due to a first trigger signal;
    successively outputting image information of a first exposed line and that of a subsequent line or lines; and
    when a number of counted external trigger signals corresponds to said predetermined number of lines exposed based on a preceding first trigger signal, setting a subsequent external trigger signal as a first trigger signal triggering an exposure of lines.

2. A method according to claim 1, wherein the image information of each successive line is output on the basis of subsequent external trigger signals.

3. A method according to claim 2, wherein a new exposure of lines is performed after a number of external trigger signals corresponding to the number of lines exposed after the preceding first trigger signal.

4. A method according to claim 3, wherein the image information of one exposed line is stored or held until it is output on the basis of the trigger signal allocated to the line.

5. A method according to claim 1, wherein a new exposure of lines is performed after a number of external trigger signals corresponding to the number of lines exposed after the preceding first trigger signal.

6. A method according to claim 1, wherein the image information of one exposed line is stored or held until it is output on the basis of the trigger signal allocated to the line.

7. An electronic camera comprising at least two lines with light-sensitive pixels, and a controller (6) that generates a set of first trigger signals based on successive external trigger signals (T1 . . . T5) spaced apart from each other, said lines are exposed based on said set of first trigger signals, said set of first trigger signals having a spacing relative to each other corresponding to a multiple of a spacing of the external trigger signals relative to each other, and said multiple corresponding to a number of lines to be exposed (a, b).

8. An electronic camera according to claim 7, further comprising an output controller that causes an output of an image information of a first exposed line (a) of the camera due to one of said first trigger signals (T1, T2, T5) and an output of an image information of a subsequently exposed line or lines (b) due to a subsequent one of said external trigger signals (T2, T4).

9. An electronic camera according to claim 8, further comprising a counting unit that counts the external trigger signals and that generates one of said first trigger signals after a number of external trigger signals corresponding to the number of exposed lines.

10. An electronic camera according to claim 8, wherein said controller generates one of said first trigger signals when image information of all of the exposed lines has been read out.

11. An electronic camera according to claim 8, wherein said controller generates one of said first trigger signals when image information of all of the exposed lines is still to be read out.

12. An electronic camera according to one of claim 8, further comprising a memory unit for storing the image information of the individual lines after an exposure according to one of said first trigger signals until it is output on the basis of the trigger signal allocated to the line and generated by the controller (6).

13. An electronic camera according to claim 7, further comprising a counting unit that counts the external trigger signals and that generates one of said first trigger signals after a number of external trigger signals corresponding to the number of exposed lines.

* * * * *